Feb. 26, 1935. S. B. FILLOW ET AL Plant Pat. 123
PANSY
Filed July 10, 1933
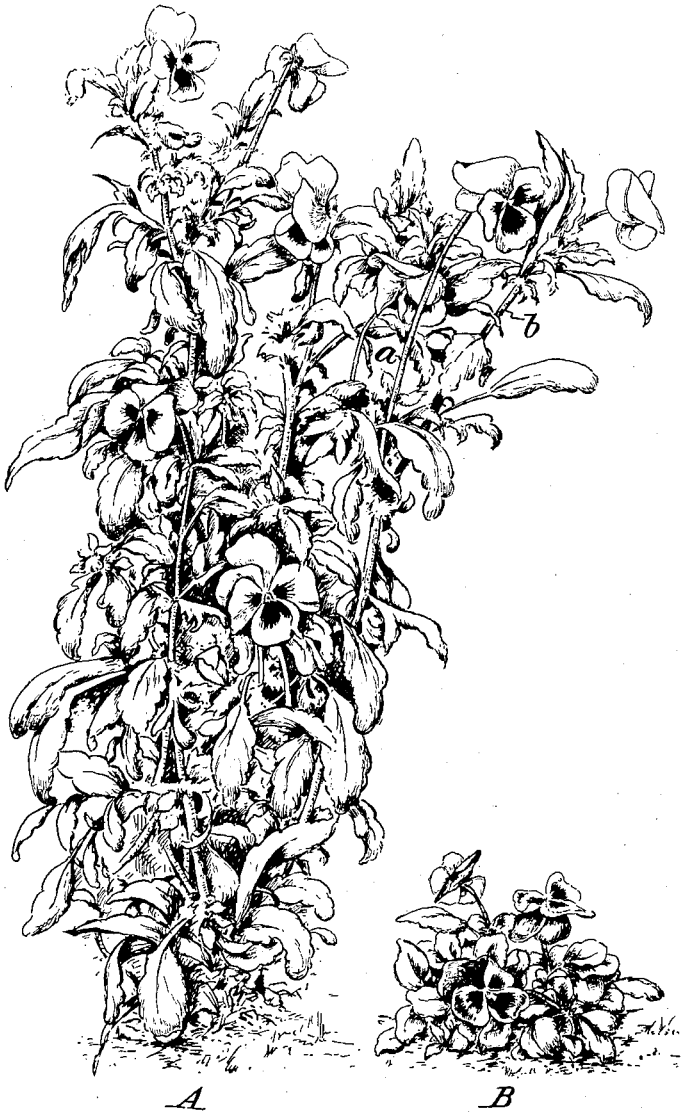
Inventors
Stanley B. Fillow
Joseph H. Sniffen
By Potter, Pierce & Scheffler
Attorneys Patented Feb. 26, 1935

Plant Pat. 123

UNITED STATES PATENT OFFICE

123

PANSY

Stanley B. Fillow and Joseph H. Sniffen,
Westport, Conn.

Application July 10, 1933, Serial No. 679,808

1 Claim. (Cl. 47—60)

Our invention relates to a new and improved form of pansy, particularly characterized by its giant habit of growth and foliage bearing qualities.

The new pansy plants have been developed by the inventors by breeding, including cross-pollination and careful selection, over a number of years, of a strain of pansies of unknown parentage in their greenhouses at Westport, Connecticut. The purpose of the development of the new pansy plant was to provide a plant of large size having the flowers borne upon long stems suitable for cut flowers.

The new plants are particularly characterized by their giant habit of growth and foliage bearing qualities; the stalks reaching a length of from 2½ to 4 feet and bearing luxuriant foliage. A typical plant of the new strain comprises 10–15 stalks.

The flowers of the new plants show all of the colors of ordinary pansy strains including solid colors and mixed or variegated colors. They attain an average diameter of 3–4 inches and are borne upon strong stems 7–12 inches long. The plants bloom very profusely, and when grown under glass they bloom freely from October to May.

The blooms may readily be cut in such a way that the stems carry a large amount of the luxurious foliage of the plant, which adds greatly to the attractiveness of the blooms and greatly enhances the value of the product.

The accompanying drawing shows at A an illustrative example of a pansy plant of the new strain, together with a typical plant of the heretofore known form of pansy at B, for comparison. The drawing, which was made from a photograph of a typical plant, shows clearly the giant habit of growth of the new plant, its luxurious foliage and free blooming characteristic.

As noted above, many of the blooms are borne upon long, strong stems from 7 to 12 inches long, as shown for example at *a*. At *b* is shown a bloom typically carried on a long stem bearing profuse foliage, affording, when cut, long-stemmed blooms set off by the accompanying foliage. These foliage-bearing flower stems are particularly characteristic of the new plant.

The new pansies may be readily propagated by the rooting of cuttings or slips. They may also be propagated from seed.

We claim:

A pansy as herein shown and described, characterized by its giant habit of growth and luxuriant foliage bearing flower stems.

STANLEY B. FILLOW.
JOSEPH H. SNIFFEN.